US006622035B1

(12) United States Patent
Merilainen et al.

(10) Patent No.: US 6,622,035 B1
(45) Date of Patent: *Sep. 16, 2003

(54) ELECTRODE FOR MEASUREMENT OF WEAK BIOELECTRICAL SIGNALS

(75) Inventors: Pekka Merilainen; Heli Tolvanen-Laakso, both of Helsinki (FI)

(73) Assignee: Instrumentarium Corp., Helsinki (FI)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/489,556

(22) Filed: Jan. 21, 2000

(51) Int. Cl.[7] ............................................. A61B 5/0408
(52) U.S. Cl. ....................... 600/391; 600/392; 607/149; 607/152
(58) Field of Search ........................ 600/372, 382–386, 600/391, 392, 395–397; 607/149, 152, 153

(56) References Cited

U.S. PATENT DOCUMENTS

| | | | |
|---|---|---|---|
| 3,505,993 A | | 4/1970 | Lewes et al. |
| 4,004,578 A | * | 1/1977 | Palmius ....................... 600/392 |
| 4,640,290 A | | 2/1987 | Sherwin |
| 4,685,466 A | | 8/1987 | Rau |
| 4,920,968 A | | 5/1990 | Takase |
| 4,969,468 A | | 11/1990 | Byers et al. |
| 5,197,471 A | | 3/1993 | Otero |
| 5,305,746 A | | 4/1994 | Fendrock |
| 5,309,909 A | | 5/1994 | Gadsby et al. |
| 5,458,141 A | | 10/1995 | Neil |
| 5,645,063 A | | 7/1997 | Straka, Jr. |
| 5,862,803 A | * | 1/1999 | Besson et al. ............... 128/903 |
| 6,132,755 A | | 10/2000 | Eicher et al. |
| 6,219,574 B1 | * | 4/2001 | Cormier et al. ................ 604/20 |
| 6,334,856 B1 | | 1/2002 | Allen et al. |

FOREIGN PATENT DOCUMENTS

| | | |
|---|---|---|
| EP | 571120 | 11/1993 |
| WO | 98/28037 | 7/1998 |
| WO | 00/74763 | 12/2000 |
| WO | 01/52731 | 7/2001 |

OTHER PUBLICATIONS

Micromachined Needles for the Transdermal Delivery of Drugs, S. Henry et al., IEEE (1998), pp. 494–499.
Electrodes and the Measurment of Bioelectric Events, Geddes, 1972, pp. 78–79 and 94–95 (Surface electrodes), pp. 4–5 (Electrode–Electrolyte Interface–Electrode Potential), pp. 8–9 (Electrode–Electrolyte Interface–Liquid–Junction Potential), pp. 10–11 (Electrode–Electrolyte Interface–Chlorided Silver Electrodes).
Barbed Spike Arrays for Mechanical Chip Attachment, Patrick Griss et al. Royal Institute of Technology, 4 pgs.
Spike Biopotentials Electrodes, Patrick Griss et al., 2000 IEEE, pp. 323–328.
Micromachined, Silicon based on Electrode Arrays for Electrical Stimunlation of or Recording From Cerebral Cortex, Richard A. Normann et al., 1991 IEEE, pp. 247–252.

* cited by examiner

Primary Examiner—Lee Cohen
(74) Attorney, Agent, or Firm—Andrus, Sceales, Starke & Sawall, LLP

(57) ABSTRACT

An electrode for acquiring bioelectrical signals employs an array of spikes that penetrate the viable epidermis layer of the skin of a patient. The spikes may be conductive to provide the bioelectrical signal. Or, the spikes may extend through a conductive layer that provides the bioelectrical signal. The signal obtained from the patient may be amplified using an amplifier and battery circuit present on the electrode body. The electrode may be used with or without conductive paste or gel.

79 Claims, 3 Drawing Sheets

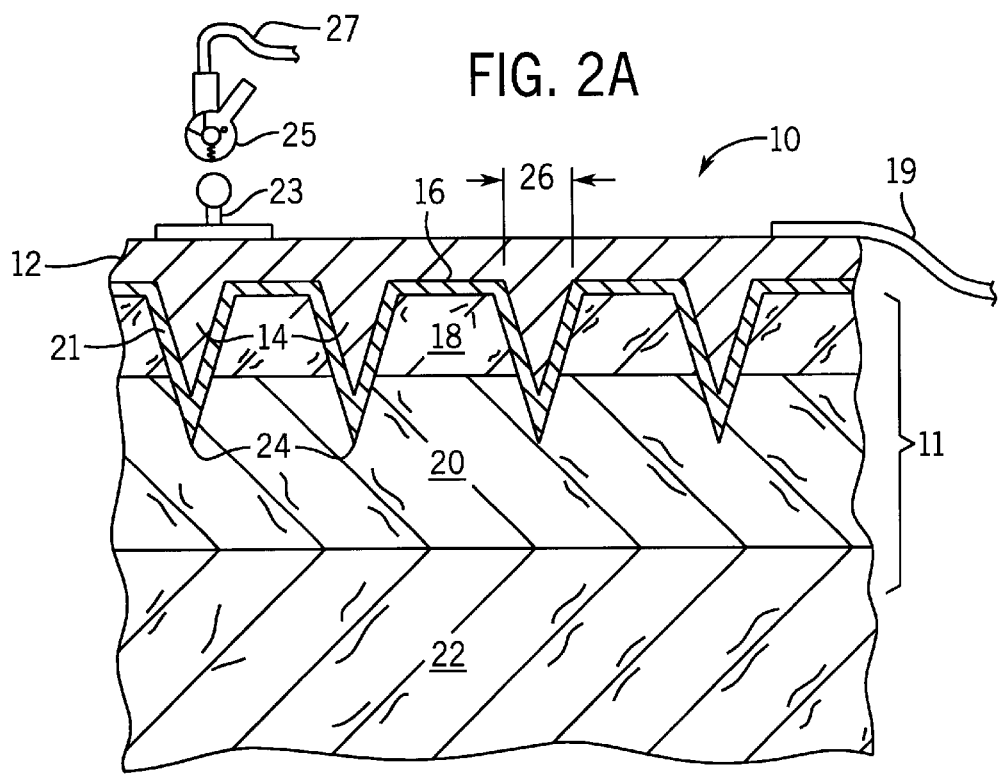
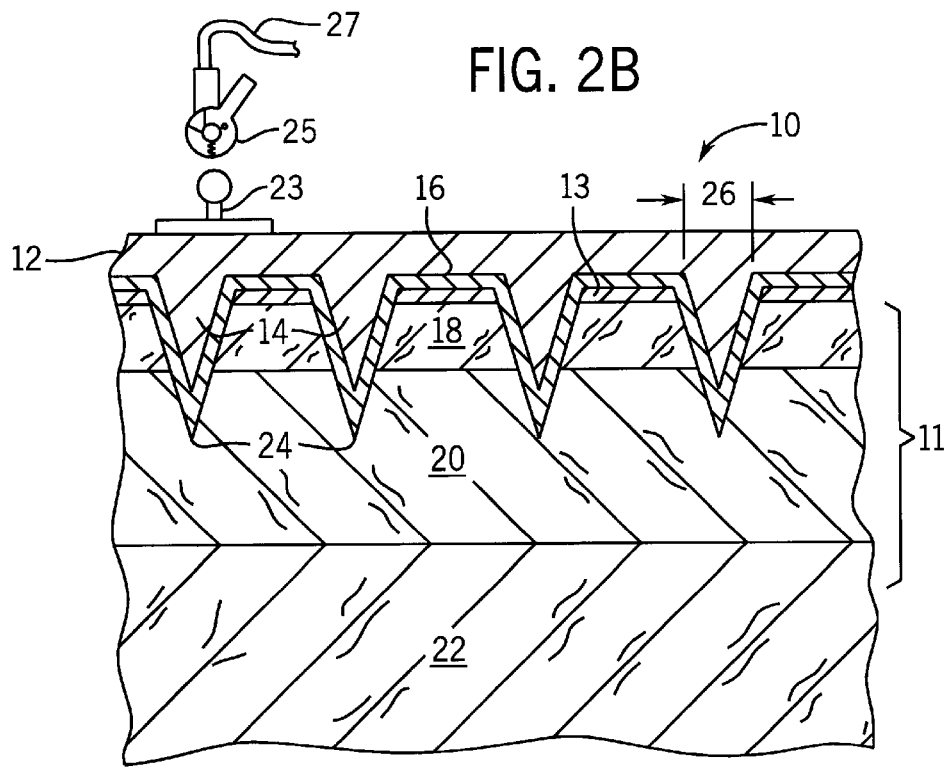

ELECTRODE FOR MEASUREMENT OF WEAK BIOELECTRICAL SIGNALS

FIELD OF THE INVENTION

The present invention relates to medical electrodes which are applied to a patient's skin for monitoring biopotentials and, in particular, to electrodes that penetrate the patient's skin to make the skin more electrically permeable.

BACKGROUND OF THE INVENTION

Diagnostic tests, treatments and the presence of illness require obtaining and monitoring electrical signals generated by the physiological functioning of a patient. Typical electrical signals or biopotentials that are commonly monitored are those producing electro-cardiograms (EKG) from the heart, electroencephalograms (EEG) from the brain and electromylograms (EMG) from muscles. Such signals are of relatively low level and may be very weak, such as the 100 microvolt or less signals present in an electroencephalogram (EEG). The frequency range of the signals extends from 0.05 for electro-cardiograms to 3000 Hz for brain stem evoked potentials.

Skin mounted monitoring electrodes are typically used to obtain the foregoing biopotentials. The human skin is made of three distinct layers; stratum corneum, viable epidermis, and dermis. The outer 10–15 micrometers of skin, called the stratum corneum, is dead tissue that forms the primary barrier for the body. The stratum corneum is the major contributor to skin impedance and to a reduction in biopotential signal magnitudes as well as a major factor in the signal to noise ratio characteristics of skin-mounted electrodes. Below the stratum corneum lies the viable epidermis (50–100 micrometers). The viable epidermis is comprised of living cells, but contains few nerves and is devoid of blood vessels. Penetration of the skin to the viable epidermis is painless since the nerves are found in deeper tissues. Below the viable epidermis is the dermis. The dermis forms the bulk of skin volume and contains living cells, nerves and blood vessels.

Difficulties often arise when measuring weak biopotentials with skin mounted electrodes. One problem is that the outermost layer of skin has a high electrical impedance. High electrical impedance reduces signal magnitude so that a data signal may be difficult to obtain when electrical noise is present.

Noise may also be injected in the biopotential signal due to movement of the skin. This results in a variation in the skin impedance. This variation in skin characteristics causes electrical noise Which is not easily separated from the biopotential data signal of interest. If the signal to noise ratio is sufficiently low, due to skin impedance or movement artifacts, it can mask or hinder correct analyses of a patient's condition.

A common practice is to abrade the stratum corneum prior to applying the biopotential electrode so as to lessen the skin impedance. The tissue so removed and skin oils are rinsed away, as with alcohol. The abraded skin is covered with an electrolytic paste and the electrode applied to the patient.

However, this procedure is time consuming, particularly when several electrodes are to be applied and is inconvenient in many clinical situations such as preparing the patient for surgery.

Piercing the skin to reduce its impedance has been suggested. A device for doing this is disclosed by Lewes et al U.S. Pat. No. 3,505,993. The Lewes et al electrode is a rigid metal sheet having an arrangement of projections or spikes. The spikes are approximately 1.5 millimeters in length, and have a base diameter of approximately 1 millimeter. The spikes press into the skin when applied, and the electrode is held in place by a rubber band or other similar means. A disadvantage of the electrode disclosed in Lewes et al is that the spikes are rather large and could be uncomfortable for the patient, as well as cause undue laceration to the skin should the electrode move with respect to the skin.

Gadsby et al U.S. Pat. No. 5,309,909 discloses a combined skin preparation and monitoring electrode wherein a plurality of tines are located on a resilient dome. The dome is held in place with an adhesive. When the dome is depressed toward the patient's skin, the tines penetrate the skin, and when pressure on the dome is released, the tines retract from the skin. Gadsby et al is disadvantageous in that one must remember to depress the resilient dome or impaired readings will be obtained. Further, this electrode requires the use of an ionic gel, and cannot be used dry.

Fendrock U.S. Pat. No. 5,305,746 discloses a disposable self-prepping electrode which utilizes an array of flexible, plastic tines which serves to part high impedance outer layers of skin to expose the low impedance, blood enriched layers without scratching or abrading. The tines are imbedded in a conductive gel layer. A center electrode stud contacts the gel and makes an electrical connection to the monitoring apparatus. The tines are between approximately 0.64 to 2.8 millimeters in length, and readily flex upon application to the skin. The Fendrock electrode is disadvantageous in that it requires use of a gel layer, and the tines may not adequately penetrate the skin due to their flexibility.

Rau U.S. Pat. No. 4,685,466 discloses a measuring sensor for biomedical signals wherein one or more short needle points penetrate the stratum corneum into approximately 10–15 cell layers from the skin surface. The Rau device does not use electrode paste or jelly. Weak signals may be improved by attaching a micro-miniaturized semiconductor arrangement directly to the electrode for active impedance matching and/or amplification. Rau is disadvantageous in that it requires a separate electrical connection for each needle. Thus, only 1–5 needles are used and the biopotential signal is extremely localized. Further, the amplification means is cumbersome because it is not part of the medical electrode itself.

BRIEF SUMMARY OF THE INVENTION

It is the object of the present invention to provide an electrode suitable for mounting on the skin of a patient and which provides an improved signal to noise ratio to the bioelectrical signal obtained by the electrode.

Another object of the present invention is to provide such an electrode which may be used without preparing the skin prior to application, and which does not require paste or gels.

A still further object of the present invention is to provide an electrode which can amplify weak bioelectrical signals.

The bioelectrical signal electrode of the present invention reduces skin impedance and movement artifacts and thus increases signal quality. The reduction/increase is obtained by the electrode through use of a spike means to penetrate the skin into the viable epidermis. The carrier for the spikes is sufficiently large that the electrode can be stably applied to the patient's skin.

Thus, and in accordance with one aspect of the invention, a bioelectric signal electrode is provided with a plurality of electrically conductive spikes that are capable of penetrating the skin to the viable epidermis layer. For this purpose, the spikes may have the necessary degree of sharpness. These spikes are attached to a carrier that allows the electrode to be applied to the surface of the human body. The bioelectrode may be kept in position using an adhesive tape or an adhesive on the periphery of the carrier. Or an electrolytic adhesive may be disposed on the underside of the carrier.

The electrode spikes range from 50–250 micrometers in length. The spikes are used in arrays of 100–10,000 spikes spaced 50–250 micrometers apart. It may be desirable to vary the spike length so that various depths of the viable epidermis layer are contacted. The base of the spikes are up to 35 micrometers in width. Sharpness in the spikes facilitates skin penetration. The size of the carrier for the spikes is typically about 25 square millimeters.

If desired, the electrode can be used with a conductive gel located between the skin and the carrier. However, a conductive gel is not always necessary, and the bioelectrode may be used dry. If conductive gel is used, it may contain antibacterial agents to prevent irritation or infection due to spike penetration of the skin.

In an alternative embodiment of the invention, the spikes are electrically nonconductive, and extend through a conductive element on the lower side of the electrode. The non-insulated spikes make the skin more permeable. An electrolytic gel or paste is used in conjunction with an electrode so constructed to make movement artifact less prominent and improve the signal to noise ratio.

When used to monitor weak biopotential signals, the bioelectric signal electrode having the aforesaid array of spikes is applied to a patient's skin so that the spikes penetrate the skin to the viable epidermis layer. Electrical leads are attached between the electrode and a monitor so that the biopotential obtained from the electrode may be amplified for display or recording.

In yet another embodiment of the present invention, an amplifier and battery are attached to the bioclectrode to boost the signal obtained from the subject. The amplifier is not activated until the bioelectrode is in use. This activation may be started by removing a protective tape from the battery and circuitry.

Various other features, objects, and advantages of the invention will be made apparent from the following detailed description and the drawings.

BRIEF DESCRIPTION OF THE SEVERAL VIEWS OF THE DRAWING

In the drawings:

FIGS. 2A and 2B are somewhat schematic, partial-section views of electrodes of the present invention showing spike elements of the electrode embedded into the skin;

DETAILED DESCRIPTION OF THE INVENTION

Figure 1:
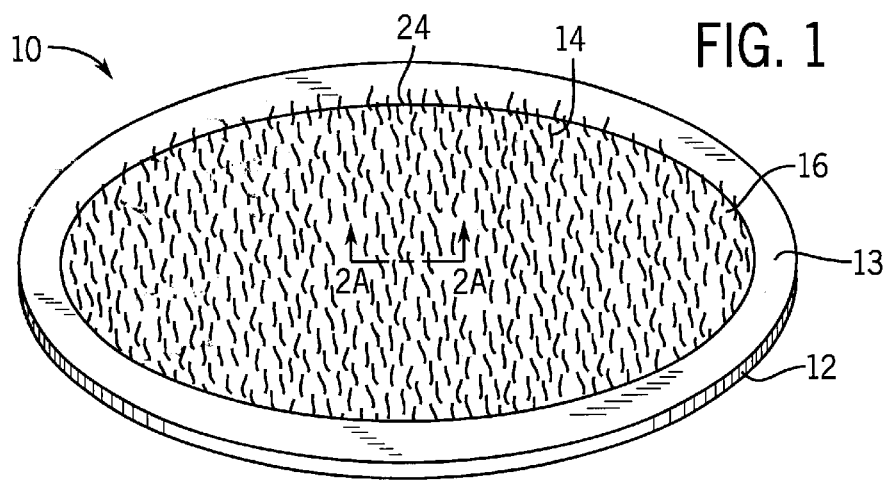
FIG. 1 is an isometric view of an electrode constructed in accordance with the present invention.

As shown in FIGS. 1, 2 and 3, electrode 10 is generally comprised of a carrier 12, having an array of spikes 14 projecting from a common surface 16.

FIG. 2A shows a schematic representation of the electrode 10 of the present invention applied to the skin 11 of the patient. Skin 11 is formed of three layers: stratum corneum 18, viable epidermis 20, and dermis 22. Stratum corneum 18 is 10–15 micrometers thick, and consists of dead tissue. Underneath stratum corneum 18 is viable epidermis 20. Viable epidermis 20 is 50–100 micrometers thick and consists of tissue containing living cells. This tissue contains few nerves, and is devoid of blood vessels. Below viable epidermis 20 is dermis 22. Dermis 22 is comprised of living cells, nerves and blood vessels.

Preferably, the spikes 14 projecting from carrier 12 penetrate skin 10 so that spike tips 24 lie within viable epidermis 20. This provides impedance reducing, electrical signal pathways across stratum corneum 18 without causing pain or bleeding of the patient. The electrode may be secured to the skin of the patient for retaining the spikes in the epidermis layer during use by adhesive tape 19. Or, a suitable adhesive 13 may be applied to the periphery of carrier 12 as seen in FIG. 1. Or, a suitable adhesive 13, preferably an electrically conductive adhesive, can be applied to or adjacent surface 16, as shown in FIG. 2B.

Each bioclectrode contains from 100–10,000 spikes 14 spaced 50–250 micrometers apart on surface 16. However, it is preferable to have a spike density of 400 to 2,000 spikes. The length of spikes ranges from 50–250 micrometers, with a preferable length of 100–200 micrometers. The base 26 of each spike is up to 35 micrometers wide. Spikes 14 may be sharp to facilitate skin penetration so that tips 24 will be substantially smaller in width than the bases. It may be desirable to vary the length of spikes 14 within any given array so that measurements are obtained from various depths of the viable epidermis rather than a constant depth. Using varied lengths of spikes 14 is advantageous because the layers of skin vary in thickness and the skin is invariably not flat.

Spikes 14 may be manufactured from metal or metal alloys (for example. silver, platinum, steel or the like), electrically conductive plastic or a semiconductor material such as silicone by micromachining.

As shown in FIGS. 2A and 2B, the surface of the spikes 14 may also be covered with a suitable material 21, such as a metal, and then coated with a suitable salt. For example, each spike 14 can be coated with silver/silver chloride layers to improve the signal to noise ratio.

The portion of electrode 10 containing spikes 14 preferably has an area of 4 square millimeters to 25 square millimeters. Typically, the area is about 25 square millimeters.

An electrical connection between electrode 10 and a bioelectrical monitor (not shown) may be achieved by a number of various means known in the art. For this purpose, electrode 10 may be provided with a projecting terminal 23. When carrier 12 is formed of conductive material, terminal 23 may be connected directly to carrier 12, as shown in FIGS. 2A and 2B. A flat, lightweight lead 27 connects one or several bioelectrodes 10 to the monitor using clip-connector 25 mating to terminal 23.

Prior to use, spikes 14 may be protected by a protective paper or film and other suitable means and/or the electrode placed in suitable packaging. The protective paper or film is removed from electrode 10 immediately before the electrode is applied to the patient's skin 11. In use, the patient's skin should preferably be relatively clean and free of excess hair in the area to which the bioclectrode will be applied. Excess hair could prevent the spikes 14 from adequately penetrating the viable epidermis. Electrode 10 is applied to skin 11 by firmly pressing down on the entire surface of bioelectrode 10, toward the patient's skin. This pressing action causes spikes 14 to engage and penetrate skin 11 as shown in FIGS. 2A and 2B, and causes the adhesive 13 to make adequate contact with the skin 11 to hold the electrode 10 in place. The electrical leads 27 are then attached to the electrodes as previously described, and to the bioelectrical monitor that records or displays bioelectrical signals.

Figure 3A:
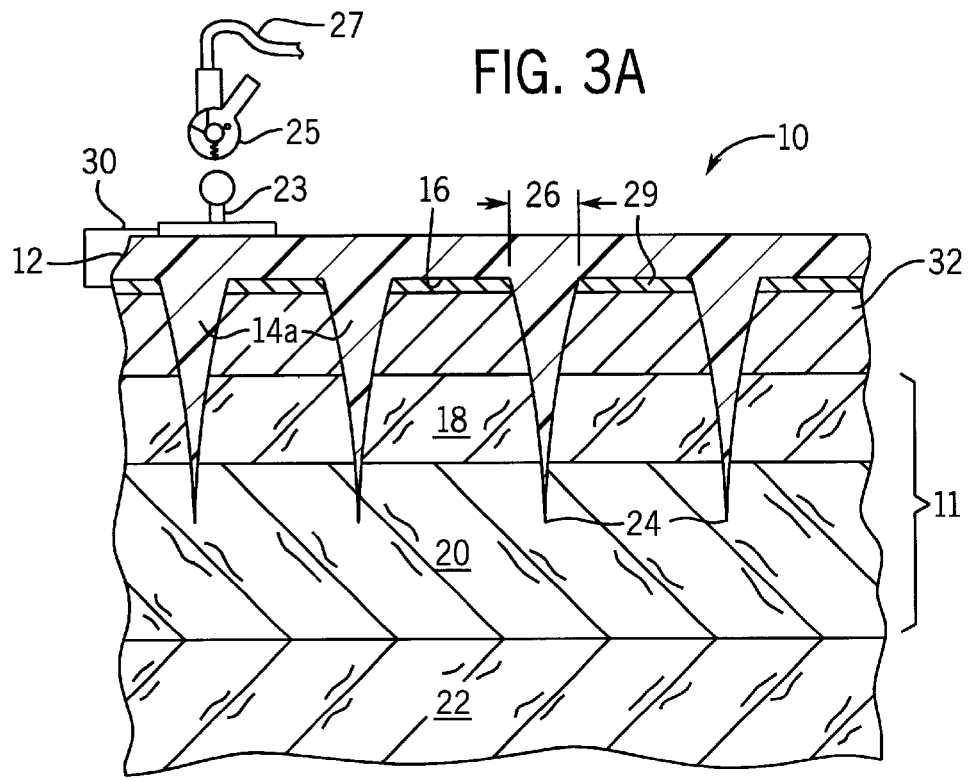
FIGS. 3A and 3B are schematic partial-section views showing an alternative embodiment of the invention.
Figure 3B:
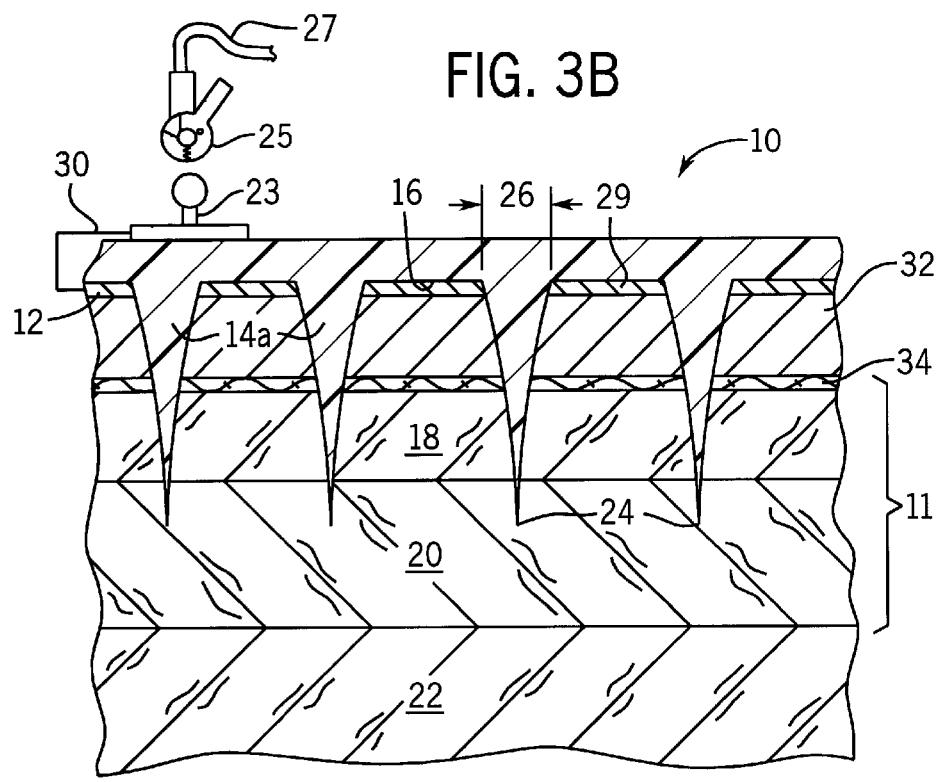

In an alternative embodiment of the present invention as shown in FIGS. 3A and 3B, electrode 10 has an electrically conductive layer 29, for instance a silver/silver chloride layer, on the lower surface of carrier 12. Spikes 14 are electrically non-conductive. In the configuration shown in FIGS. 3A and 3B, spikes 14 are shown as integrally formed with a non-conductive carrier 12. However, spikes 14 may be formed as separate elements and attached to the carrier, if desired. Electrically conductive layer 29 may be connected to terminal 23 by conductor 30.

A conductive medium, such as electrolytic paste 32, may be interposed between electrically conductive layer 29 and skin 11 of the patient. The increased permeability of the skin arising from the penetration of spikes 14 improves electrode-skin coupling through the electrolytic paste. The use of the electrolytic paste reduces movement artifacts because the paste is inherently flexible and unaffected by slight mechanical disturbances. Paste 32 may contain antibacterial agents, if desired.

As shown in FIG. 3B, a retainer 34 in the form of a net or screen can be used to retain the electrolytic paste on electrode 10 and to prevent undue spreading of the paste when the electrode is applied to the skin of the patient. The retainer 34 is preferably a plastic material which may be placed over the spikes 14 to hold a paste or gel in the area of spikes 14. The plastic material is such that it compresses when the electrode is placed on the patient, and does not interfere with spike 14 penetration of the skin. The electrolytic paste passes through the screen into contact with the skin of the patient.

While spikes 14 may be embedded in the skin when the bioelectrical signal is being obtained, it is also possible to momentarily press the spikes into the skin to increase the permeability of the skin and thereafter release the electrode allowing the spikes to withdraw from the skin while the signal is being obtained. In this particular embodiment, a carrier 12 is normally biased so that after the bioelectrode 10 is depressed, it springs back to an original shape. The springing action causes the spikes 14 to withdraw from the skin 11. In this embodiment, a conductive medium such as electrolytic paste 32 is necessary to create the electrode-skin coupling.

Figure 4A:
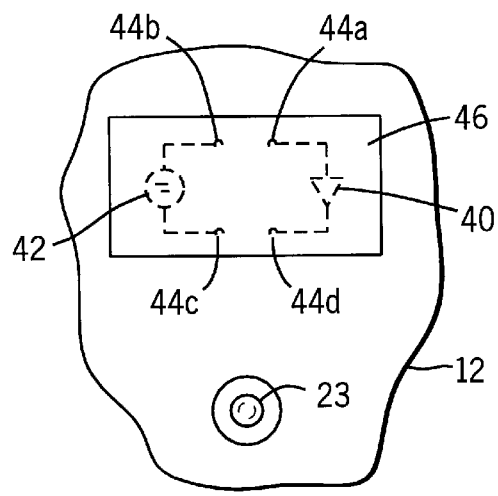
FIGS. 4A, 4B, and 4C are schematic views showing further alternative embodiments of the invention.
Figure 4B:
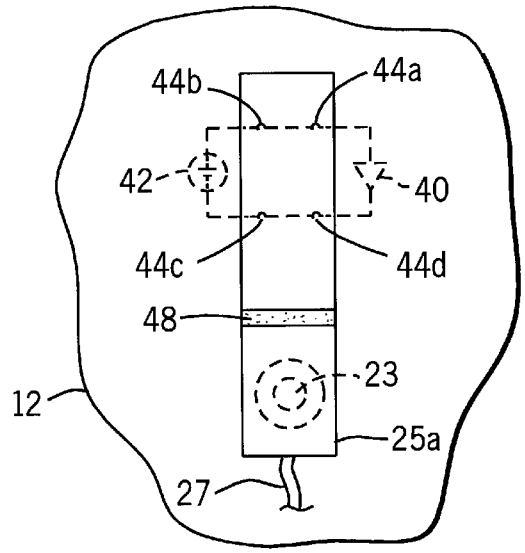
Figure 4C:
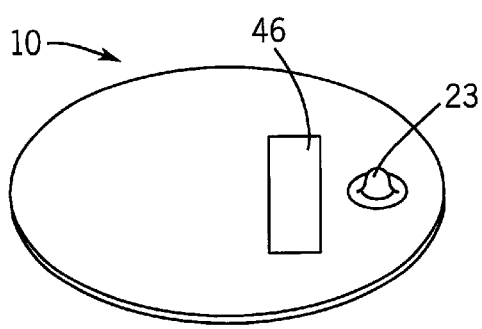

In another embodiment of the present invention, as shown in FIGS. 4A to 4C, an amplifier 40 is used to boost the signal obtained by the electrode 10. Amplifier 40 is energizable by battery 42 and both elements can be incorporated in carrier 12. In order to avoid draining the battery, the connection between the amplifier and battery is not made until the bioelectrode 10 is in actual use. As shown in FIG. 4A there are interrupted connections at nodes 44a–d on the surface of carrier 12. The exposed nodes are covered with tape 46. As seen in FIG. 4b, clip-connector 25a, is formed so that when it is attached to the electrode terminal 23, nodes 44a–d and nodes 44c–d are bridged by conductive elements in the connector. In other words, a clip-connector 25a electrically connects the amplifier 40 to the battery 42 when a connection is made with terminal 23. Insulator 48 separates the portion bridging nodes 44a–d from that connecting with terminal 23.

To prevent accidental connection between nodes 44a–d or contact with battery 42, the piece of tape 46 remains across the nodes, as shown in FIG. 4C, until the electrode 10 is placed on the patient, at which time it is peeled away.

Although the invention has been illustrated as described in terms of certain embodiments, it should be understood that other variations will be apparent to those skilled in the art. For instance, one skilled in the art would readily recognize that electrodes 10 may be used with animals.

It is recognized that other equivalents, alternatives, and modifications aside from those expressly stated, are possible and within the scope of the appended claims.

What is claimed is:

1. An electrode for obtaining a biopotential signal from the skin of a subject, said electrode comprising:

a carrier having a surface positioned contiguous with the skin of the subject when the electrode is applied to the subject's skin;

a plurality of spikes extending from said surface of said carrier for being inserted into and below the surface of the skin of the subject when the electrode is applied to the subject's skin, said carrier and spikes presenting electrically conductive surfaces to tissue of the subject's skin over essentially the entirety of the elements so as to optimize the extent of the conductive surface area, said spikes having a length of 50 –250 μm for extending into the viable epidermis layer of the skin when the electrode is applied to the subject's skin, said electrode having between 100 and 10,000 spikes on said carrier surface, the optimized conductive surface area of the carrier and spikes increasing the effective contact area with the subject's skin for reducing the biopotential signal impedance; and a connector for obtaining said biopotential signal and for making the signal available externally of the electrode.

2. The electrode of claim 1 wherein said spikes are arranged in an array and spaced 50 to 250 micrometers apart on said carrier.

3. The electrode of claim 1 wherein the length of the spikes is varied.

4. The electrode of claim 1 wherein spikes are tapered from a base to a tip to facilitate skin penetration.

5. The electrode of claim 4 wherein the spikes have bases adjacent said surface of said carrier and wherein said bases are up to 35 micrometers in width.

6. The electrode of claim 1 wherein the length of the spikes ranges from 100 to 200 μm.

7. The electrode of claim 1 wherein the number of spikes is 400–2000 spikes.

8. The electrode of claim 1 further including adhesive for securing the electrode to the skin of the subject.

9. The electrode of claim 8 wherein the adhesive comprises an adhesive tape.

10. The electrode of claim 8 wherein the adhesive is applied to said surface of the carrier.

11. The electrode of claim 10 wherein the adhesive is electrically conductive.

12. The electrode of claim 1 wherein the area of said surface of said carrier ranges from 4 to 25 square millimeters.

13. The electrode of claim 1 further including a conductive layer located on the surface of said spikes and carrier.

14. The electrode of claim 13 further including a conductive medium located between said conductive layer and the skin.

15. The electrode of claim 14 wherein the conductive medium contains antibacterial agents.

16. The electrode of claim 14 further including a retainer for retaining the conductive medium on the conductive layer.

17. The electrode of claim 1 further including an amplifier for boosting the biopotential signal obtained from the subject.

18. The electrode of claim 17 wherein the amplifier is powered by a battery.

19. The electrode of claim 18 wherein said amplifier and battery are incorporated in said carrier.

20. The electrode of claim 18 wherein an open electrical circuit between the amplifier and battery is maintained by placing a removable tape across the battery and the open electrical circuit.

21. The electrode of claim 20 wherein the open electrical circuit is closed with a connection means after said tape is removed.

22. The electrode of claim 1 wherein said electrode is of unitary construction and the spikes and the carrier are made from a common material.

23. An electrode for obtaining a biopotential signal from the skin of a subject, said electrode comprising:
- a carrier having a surface positioned contiguous with the skin of the subject when the electrode is applied to the subject's skin, said carrier being electrically conductive on said surface;
- a plurality of spikes, each spike having a base joined to said carrier, said spikes extending from said surface of said carrier for being inserted into and below the surface of the skin of the subject when the electrode is applied to the subject's skin, said spikes being electrically non-conductive and having a length of 50–250 $\mu$m for extending into a viable epidermis layer of the skin when the electrode is applied to the subject's skin; and
- a connector coupled to said conductive surface for obtaining said biopotential signal and for making the signal available externally of the electrode.

24. The electrode of claim 23 wherein the plurality of spikes comprise 100 to 10,000 spikes.

25. The electrode of claim 23 wherein said plurality of spikes comprise 100 to 10,000 spikes and the area of said surface of the carrier is 4 to 25 square millimeters.

26. The electrode of claim 23 wherein said spikes are arranged in an array and spaced 50 to 250 micrometers apart on said carrier.

27. The electrode of claim 23 wherein the length of the spikes is varied.

28. The electrode according to claim 23 wherein spikes are tapered from a base to a tip to facilitate skin penetration.

29. The electrode of claim 28 wherein the spikes have bases adjacent the surface of the carrier and wherein said bases are up to 35 micrometers in width.

30. The electrode of claim 23 further including a conductive layer located on the surface of said carrier.

31. The electrode of claim 30 further including a conductive medium located between said conductive layer and the skin.

32. The electrode of claim 31 wherein the conductive medium contains antibacterial agents.

33. The electrode of claim 31 further including a retainer for retaining the conductive medium on the conductive layer.

34. The electrode of claim 24 wherein the plurality of spikes comprise 400–2000 spikes.

35. The electrode of claim 23 wherein said carrier is electrically non-conductive.

36. The electrode of claim 23 wherein the area of said surface of the carrier ranges from 4 to 25 square millimeters.

37. The electrode of claim 23 wherein the spikes have a length of 100–200 $\mu$m.

38. The electrode of claim 23 further including adhesive for securing the electrode to the skin of the subject.

39. The electrode of claim 38 wherein said adhesive is disposed on the carrier for securing the electrode to the skin of the subject.

40. The electrode of claim 39 wherein the adhesive disposed on the carrier is applied to the carrier.

41. The electrode of claim 39 wherein the adhesive is electrically conductive.

42. The electrode of claim 39 wherein the adhesive disposed on the carrier comprises an adhesive tape.

43. The electrode of claim 23 further including an amplifier for boosting the biopotential signal obtained from the subject.

44. The electrode of claim 43 wherein the amplifier is powered by a battery.

45. The electrode of claim 44 wherein said amplifier and battery are incorporated in said carrier.

46. The electrode of claim 44 wherein an open electrical circuit between the amplifier and battery is maintained by placing a removable tape across the battery and the open electrical circuit.

47. The electrode of claim 46 wherein the open electrical circuit is closed with a connection means after said tape is removed.

48. The electrode of claim 23 wherein said electrode is of unitary construction and the spikes and the carrier are made from a common material.

49. An electrode for obtaining a biopotential signal from the skin of a subject, said electrode comprising:
- a carrier having a surface positioned contiguous with the skin of the subject when the electrode is applied to the subject's skin, said carrier having an area ranging from 4 to 25 square millimeters, said carrier being electrically conductive on said surface;
- a plurality of spikes extending from said surface of said carrier for being inserted into and below the surface of the skin of the subject when the electrode is applied to the subject's skin, said spikes being electrically non-conductive, said electrode having between 100 and 10,000 spikes on said carrier surface; and
- a connector coupled to said conductive surface for obtaining said biopotential signal and for making the signal available externally of the electrode.

50. The electrode of claim 49 wherein said spikes are arranged in an array and spaced 50 to 250 micrometers apart on said carrier.

51. The electrode of claim 49 wherein the length of the spikes ranges from 50 to 250 micrometers.

52. The electrode of claim 51 wherein the length of the spikes is varied.

53. The electrode of claim 51 wherein the length of the spikes ranges from 100 to 200 $\mu$m.

54. The electrode of claim 49 wherein the length of the spikes is varied.

55. The electrode according to claim 49 wherein spikes are tapered from a base to a tip to facilitate skin penetration.

56. The electrode of claim 55 wherein the spikes have bases adjacent the surface of the carrier and wherein said bases are up to 35 micrometers in width.

57. The electrode of claim 49 further including a conductive layer located on the surface of said carrier.

58. The electrode of claim 57 further including a conductive medium located between said conductive layer and the skin.

59. The electrode of claim 58 wherein the conductive medium contains antibacterial agents.

60. The electrode of claim 58 further including a retainer for retaining the conductive medium on the conductive layer.

61. The electrode of claim 49 wherein said carrier is formed of an electrically non-conductive material.

62. The electrode of claim 49 wherein said electrode has between 400 and 2000 spikes on said carrier surface.

63. An electrode of claim 49 further including adhesive for securing the electrode to the skin of the subject.

64. The electrode of claim 63 wherein said adhesive is disposed on the carrier for securing the electrode to the skin of the subject.

65. The electrode of claim 64 wherein the adhesive disposed on the carrier comprises an adhesive tape.

66. The electrode of claim 64 wherein the adhesive disposed on the carrier is applied to the carrier.

67. The electrode of claim 64 wherein the adhesive is electrically conductive.

68. The electrode of claim 49 further including an amplifier for boosting the biopotential signal obtained from the subject.

69. The electrode of claim 61 wherein the amplifier is powered by a battery.

70. The electrode of claim 69 wherein said amplifier and battery are incorporated in said carrier.

71. The electrode of claim 69 wherein an open electrical circuit between the amplifier and battery is maintained by placing a removable tape across the battery and the open electrical circuit.

72. The electrode of claim 71 wherein the open electrical circuit is closed with a connection means after said tape is removed.

73. The electrode of claim 49 wherein said electrode is of unitary construction and the spikes and the carrier are made from a common material.

74. A method for obtaining biopotential signals from a subject comprising the steps of:
   (a) applying an electrode having an array of spikes to the subject's skin, the spikes being electrically non-conductive having a length of 50–250 $\mu$m for penetrating into the skin to the viable epidermis, the electrode having between 100 and 10,000 spikes mounted on a carrier, the carrier and spikes presenting electrically conductive surfaces to the subject's skin, the electrode having an electrical lead;
   (b) establishing an electrical signal path from the skin to the conductive surfaces of the electrode; and
   (c) obtaining the biopotential signals from the electrical lead.

75. The method of claim 74 further including the step of fastening the electrode to the subject's skin.

76. A method for obtaining biopotential signals from a subject comprising the steps of:
   (a) applying an electrode having an array of spikes to the subject's skin, the spikes having a length of 50–250 $\mu$m for penetrating into the skin to the viable epidermis, the spikes being electrically non-conductive and mounted on a carrier having a conductive surface positioned contiguous with the subject's skin, the electrode having an electrical lead;
   (b) establishing an electrical signal path from the skin to the conductive surface to the carrier; and
   (c) obtaining the biopotential signals from the electrical lead.

77. The method of claim 76 further including the step of fastening the electrode to the subject's skin.

78. A method for obtaining biopotential signals from a subject comprising the steps of:
   (a) applying a electrode having an array of spikes to the subject's skin so that the spikes penetrate the skin to the viable epidermis, the electrode having between 100 and 10,000 electrically non-conductive spikes extending from an electrically conductive surface of a carrier, the surface having an area of 4 to 25 square millimeters, the electrode having an electrical lead;
   (b) establishing an electrical signal path from the skin to the conductive surface of the carrier; and
   (c) obtaining the biopotential signals from the electrical lead.

79. The method of claim 78 further including the step of fastening the electrode to the subject's skin.

* * * * *